United States Patent [19]

Janoski et al.

[11] 4,177,217

[45] Dec. 4, 1979

[54] CONTINUOUS PROCESS FOR CONVERSION OF DIMETHYLDICYCLOPENTADIENE TO ENDO-DIMETHYLDICYCLOPENTADIENE, A MISSILE FUEL

[75] Inventors: Edward J. Janoski, Havertown; Richard E. Mitchell, Boothwyn; Abraham Schneider, Overbrook Hills, all of Pa.

[73] Assignee: Suntech, Inc., Philadelphia, Pa.

[21] Appl. No.: 837,127

[22] Filed: Sep. 28, 1977

[51] Int. Cl.$^2$ .............................................. C07C 13/00
[52] U.S. Cl. ..................................... 585/253; 60/208; 149/109.4; 149/109.6; 585/14; 585/21; 585/276; 585/360
[58] Field of Search ..................... 260/666 D, 666 PY; 60/208; 149/109.4, 109.6

[56] References Cited

U.S. PATENT DOCUMENTS 3,381,046  4/1968  Cohen ........................... 260/666 PY

*Primary Examiner*—Veronica O'Keefe
*Attorney, Agent, or Firm*—J. Edward Hess; Donald R. Johnson; Anthony Potts, Jr.

[57] ABSTRACT

Dimethyldicyclopentadiene is continuously hydrogenated to tetrahydrodimethyldicyclopentadiene and then the latter is continuously isomerized to a missile fuel. Both the hydrogenation and the isomerization steps use a nickel on silica-alumina catalyst. The temperature of the hydrogenation is in the range of about 70°–260° C., and the temperature of the isomerization is in the range of about 200°–280° C. The space velocity of the hydrogenation is about 0.1 to about 2.0 volumes of the diene charged per volume of catalyst per hour and the space velocity of the isomerization is about 0.1 to about 3.0 volumes of the hydrocarbon charged per volume of catalyst per hour. The pressure range for hydrogenation is between about 200 psig to about 3000 psig and for isomerization between from about 10 psig to about 1500 psig. Hydrogen is present during the isomerization.

5 Claims, 1 Drawing Figure

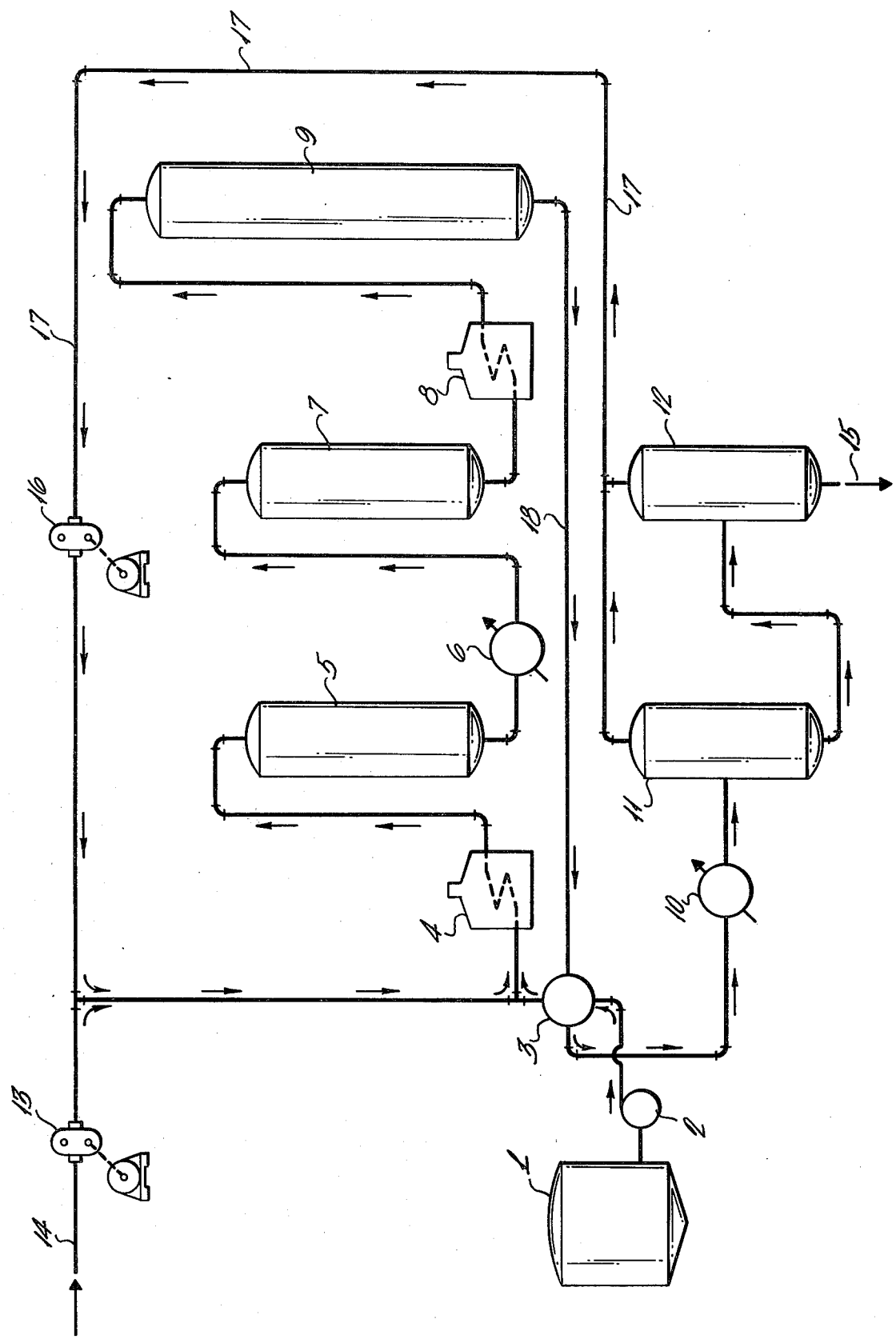

CONTINUOUS PROCESS FOR CONVERSION OF DIMETHYLDICYCLOPENTADIENE TO ENDO-DIMETHYLDICYCLOPENTADIENE, A MISSILE FUEL

BACKGROUND OF THE INVENTION

The invention herein described was made in the course of or under a contract thereunder with the United States Air Force Systems Command.

The invention relates to a continuous process for the catalytic hydrogenation of dimethyldicyclopentadiene to tetrahydrodimethyldicyclopentadiene and the catalytic isomerization of the latter to a liquid mixture of isomers. The resulting liquid mixture of isomers has a high density and good low temperature viscosity. Hereinafter the dimethyldicyclopentadiene shall be referred to as DMDCP and the tetrahydrocimethyldicyclopentadiene shall be referred to as THDMDCP.

The aforementioned resulting isomeric liquid mixture can be used as high energy missile fuel. Such fuels can be used in either jet or rocket propulsion. Jet propulsion includes a jet engine which can be used for a missile, an aircraft and others and includes the three basic types, i.e., ramjet, turbo-jet and pulse jet. The term rocket generally refers to a device containing its own oxygen or oxidizing agent. An article in Aviation Week and Space Technology, Jan. 26, 1976, pages 111–113, discloses some of the high density hydrocarbon fuels that are under consideration as missile fuels.

DMDCP is prepared by dimerizing methylcyclopentadiene. The resulting dimer mixture contains many isomers some of which can be represented by the following structures:

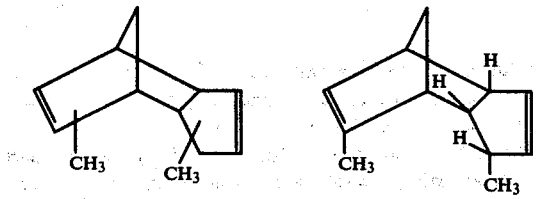

The foregoing structures are considered to have an endo structure, i.e., the methyl groups, for example are pointing in a direction opposite of the bridge.

Some of the hydrogenated isomers are known to have substantially different melting points. For example the following two isomers are a clear liquid at ambient temperature:

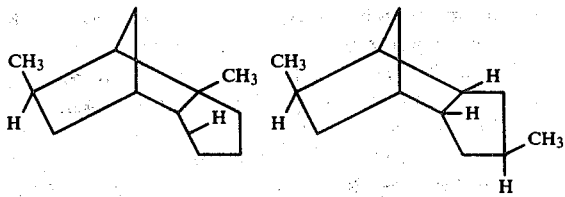

whereas the following two isomers are solid at room temperature:

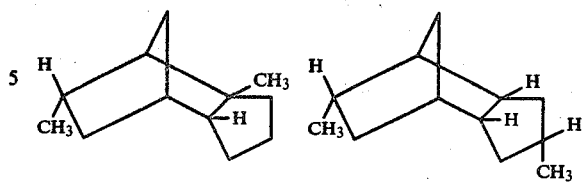

Thus, the problem is how to isomerize the isomeric mixture from one which is not suitable as a missile fuel to an isomeric liquid mixture that is suitable.

SUMMARY OF THE INVENTION

DMDCP is continuously hydrogenated to THDMDCP by contacting it with a nickel on silica-alumina catalyst at a temperature within a range of about 70° C.–260° C. and with a space velocity of about 0.1 to 2.0 volume of diene charged per volume of catalyst per hour. Then the THDMDCP is continuously isomerized to a liquid mixture of isomers by contacting it with a nickel on silica alumina catalyst at a temperature within a range of about 200° C.–280° C. and with a space velocity of about 0.1 to about 3.0 volume of THDMDCP charged per the volume of catalyst per hour. The hydrogenation pressure range is between from about 200 psig to about 3000 psig and the isomerization pressure range is between from about 10 psig to about 1500 psig. The isomerization results in a liquid mixture having low temperature properties making it suitable for use as a missile fuel.

DESCRIPTION

The accompanying FIGURE illustrates schematically one embodiment of the process.

Referring to the FIGURE storage means 1 contains the DMDCP. The latter is moved from storage means 1 by pump 2 through heat exchanger 3, and then to heater 4 along with makeup hydrogen 14 and recycle hydrogen 17. The amount of hydrogen used is related to the amount of hydrocarbon feed, thus the moles of hydrogen per mole of DMDCP feed is in the range between from about 5 to about 40 at the point of entry to contacting means 5. The DMDCP is heated in exchanger 3 by transfer of heat obtained by cooling reaction product 18 from isomerization means 9. In heater 4 the temperature of the DMDCP is raised to a temperature within a range of between from about 70° C. to about 160° C. Upon leaving heater 4, the DMDCP enters contacting means 5 containing the nickel on silica-alumina catalyst. The space velocity of the DMDCP in contacting means 5 ranges between from about 0.1 to about 2.0 volumes of cold liquid DMDCP per volume of the nickel on silica-alumina catalyst per hour. During the contacting in means 5 the hydrogenation of the double bonds of the dienes occur. Since the hydrogenation is exothermic the scheme in the FIGURE involves that only a portion of the hydrogenation occurs in the first contacting means (5) and the product therefrom is cooled in exchanger 6 (to remove heat of reaction) before completing the hydrogenation in contacting means 7 at a temperature range between from about 140° C. to about 260° C. Generally the isomerization is higher than the hydrogenation temperature, but some overlap can occur. The operating conditions of contacting means 7 is similar to that of contacting means 5 except a slightly higher temperature is used since the second double bond is somewhat more difficult to hydrogenate. Contacting means 5 and 7 can be a fixed bed reactor or a trickle bed reactor. While two contacting means, 5 and 7, are shown other alternatives are feasible e.g., one reactor with internal coolers. Also more than two contacting means can be used.

The pressure of the hydrogenation can vary substantially. The upper pressure limit is usually determined by economics and/or equipment limitations whereas the low pressure is controlled by the rate of hydrogenation. A preferred range of pressure is between from about 200 psig to about 3000 psig with about 250 psig to about 2500 more preferred.

After leaving contacting means 7 the temperature of the product mixture in heater 8, is raised to a range between from about 200° C. to about 280° C. The heated mixture from heater 8 is sent to isomerizing means 9. In isomerizing means 9 the THDMCP contacts nickel on silica-alumina catalyst. During the contacting, and in the presence of hydrogen, the THDMDCP isomers are converted to THDMDCP isomers which have a low temperature viscosity and other properties making it useful as a missile fuel. The amount of hydrogen present can vary substantially. In this embodiment the amount of hydrogen depends on how much is sent to the heater 4 and how much is consumed during hydrogenation. Its function is to keep the catalyst active and free of any carbon. The space velocity of the THDMDCP in means 9 ranges between from about 0.1 to about 3.0 volumes of THDMDCP to volume of nickel on silica-alumina catalyst per hour.

The pressure during the isomerization can vary over a wide range. A nominal amount of pressure is useful and assists in favoring the isomerization. A preferred range of pressure during isomerization is between from about 10 psig to about 1500 psig.

The resulting liquid isomeric mixture 18 leaves isomerizing means 9 and is cooled by passing it through exchanger 3 which transfers heat to the incoming fresh DMDCP. The isomeric mixture 18 is further cooled by cooling means 10 and then is sent to a high pressure separating means 11. In separating means 11 some of the unused hydrogen is separated and becomes part of recycle 17. From the high pressure separating means 11 the product is sent to low pressure separating means 12 where the balance of the unused hydrogen is separated to become part of recycle 17. While two separating means are shown other alternatives are feasible. Pressuring means 16 raises the pressure of the recycle hydrogen to a suitable level whereas pressuring means 13 raises the pressure of incoming makeup hydrogen 14.

While the DMDCP feed can contain other similar hydrocarbons, such hydrocarbons should not adversely effect either the hydrogenation reaction or the isomerization reaction. Further any of the similar hydrocarbons should not adversely influence the desired resulting properties of the saturated isomeric mixture. Thus, for optimum results the feed consists essentially of DMDCP which itself can be a mixture of DMDCP isomers.

The hydrogenation of one of the isomers of DMDCP via present invention can be represented by the following formula reaction:

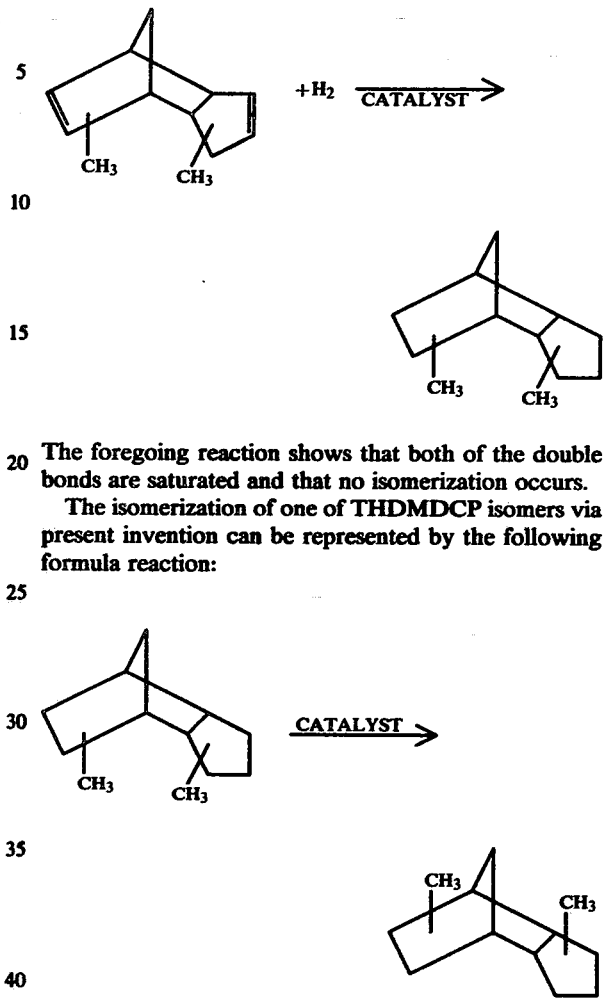

The foregoing reaction shows that both of the double bonds are saturated and that no isomerization occurs.

The isomerization of one of THDMDCP isomers via present invention can be represented by the following formula reaction:

The foregoing reaction shows that the one result of the isomerization is to convert methyl group in the endo position to those in the exo position.

The catalyst used in both the hydrogenation and isomerization is a nickel on silica-alumina. The amount of nickel on the silica-alumina carrier can vary substantially e.g., from about 0.5 weight percent to about 80 weight percent while a preferred range is between from about 40 weight percent to about 70 weight percent. The silica-alumina weight ratio of the catalyst can also vary substantially, e.g., in the range between from about 1:30 to about 30:70.

The properties of the resulting isomerized liquid mixture can vary substantially depending upon the amount of isomerization that occurs. It can depend, in addition to the composition of the initial mixture, on how much of each of the particular isomer of THDMDCP is present. Typically the resulting isomerized THDMDCP mixture will have a density (20°/4 C.) in the range between from about 0.911 to about 0.914. As to viscosity the isomeric mixture will have a kinematic viscosity at 100° F. in the range between from about 2 cst to about 3 cst.

To further illustrate the process the following example is provided.

EXAMPLE

Commercially available DMDCP along with hydrogen was fed to a ½"O.D. reactor tube having the following configuration. The first 5 3/16" of the reactor, (the top) was packed with crushed alumina (12-16 mesh): its purpose was to provide a zone for preheating and even distribution of the DMDCP feed. The next 4 ⅛" of the reactor tube was filled with nickel (60%) on kieselguhr (12-16 mesh) and amounted to 13.4 grams and occupied 10 cc. The last 3 1/16" of the reactor was filled with crushed tabular alumina (12-16 mesh); its function was to provide a means of support for the active catalyst zone.

The temperature of the DMDCP feed and hydrogen just before entering the top reactor was 330° F. (~165° C.) and the pressure was 350 psig. The mole ratio of the hydrogen to DMDCP was 20/1. The DMDCP was charged at the hourly rate of one volume of cold liquid DMDCP to one volume of catalyst. The hydrogenation was exothermic and as a result temperatures of 385°-400° F. (195°-204° C.) were observed in the reactor. The material leaving the reactor was analyzed by vapor phase chromatography (vpc) as essentially THDMDCP.

The isomerization of the THDMDCP was carried out in the previously described reactor. The THDMDCP, along with hydrogen, was charged to the reactor at a pressure of 400 psig. Several runs were made at different temperatures and different space velocities. The aforementioned values are as follows:

| Run | Temperature °C. | Space Velocity |
|-----|-----------------|----------------|
| 1   | 240             | 1.0            |
| 2   | 260             | 0.5            |
| 3   | 220             | 0.5            |
| 4   | 260             | 1.5            |
| 5   | 220             | 0.5            |

Using run 1 as a base the product from run 2 was the least dense and the least viscous and suggested that some cracking to a lighter material occured. Again using run 1 as a base, the product from run 5 was more dense. Runs 3 and 4, compared to run 1, showed different amounts of the various isomers. The foregoing changes in the relative amount of the isomers were determined by vpc and demonstrated that the composition of the isomeric product can be varied over a wide range.

The isomeric products from runs 1 5, compared to commercially available unisomerized THDMDCP, was superior in having both better (lower) viscosities and freezing points. The unisomerized THDMDCP contained relatively large amounts of the two highest boiling THDMDCP isomers which are solid at room temperature and tend to elevate the freezing point and increase the low temperature viscosity of the mixture. In contrast the isomeric mixtures from runs 1-5, as determined by vpc contained substantially less quantities of the aforementioned two highest boiling isomers.

Both the hydrogenation and isomerization can be carried out at temperatures, pressures and space velocities other than those used and analogous results will be obtained. Also similar results will be obtained if a catalyst is used which contains a different amount of nickel then that previously mentioned.

The invention claimed is:

1. Process for the continuous conversion of endodimethyldicyclopentadiene to exo-tetrahydrodimethyldicyclopentadiene comprising:

a. hydrogenating endo dimethyldicyclopentadiene by contacting the diene with nickel on a silica-alumina catalyst wherein the volume of the diene charged to the volume of the catalyst per hour is in the range from about 0.1 to about 2.0 and the moles of hydrogen present per mole of the diene is in the range from about 5 to about 40 and the contacting temperature is in the range of between from about 165° C. to about 204° C. and the pressure is in the range from about 200 psig to about 3000 psig and continuing the contacting until the diene is hydrogenated to tetrahydrodimethyldicyclopentadiene; and b. isomerizing, in the presence of hydrogen, the tetrahydrodimethyldicyclopentadiene by contacting it with nickel on a silica-alumina catalyst wherein the volume of the tetrahydrodimethyldicyclopentadiene charged to the volume of the catalyst per hour is in the range from about 0.1 to about 3.0 and the contacting temperature is in the range from about 220° C. to about 260° C., and the pressure is in the range from about 10 psig to about 1500 psig and continuing the contacting of the tetrahydrodimethyldicyclopentadiene until exo-tetrahydrodimethyldicyclopentadiene is formed.

2. Process according to claim 1 wherein the catalyst contains from about 0.5 weight % to about 80 weight % of nickel.

3. Process according to claim 2 wherein the silica-alumina weight ratio is in the range between from about 1:30 to about 30:70.

4. Process according to claim 1 wherein the endodimethyldicyclopentadiene formed is a missile fuel and has a density (20°/4 C.) in the range from about 0.911 to about 0.914.

5. Process according to claim 4 wherein the missile fuel has a kinematic viscosity at 100° F. in the range between from about 2 cst to about 3 cst.

* * * * *